United States Patent [19]

Christman et al.

[11] 4,331,809
[45] May 25, 1982

[54] CARBAMYLBIURET-MODIFIED POLYISOCYANATES

[75] Inventors: Donald L. Christman, Grosse Ile; Peter T. Kan, Plymouth, both of Mich.

[73] Assignee: BASF Wyandotte Corporation, Wyandotte, Mich.

[21] Appl. No.: 220,592

[22] Filed: Dec. 22, 1980

Related U.S. Application Data

[63] Continuation-in-part of Ser. No. 92,479, Nov. 8, 1979, Pat. No. 4,271,087.

[51] Int. Cl.³ .................................................. C07D 237/16
[52] U.S. Cl. ...................................... 544/238; 544/240
[58] Field of Search ................................ 544/240, 238

[56] References Cited

U.S. PATENT DOCUMENTS 3,350,193 10/1967 Reicheneder et al. ......... 544/240 X
3,441,588 4/1969 Wagner et al. ............... 260/455 AB

FOREIGN PATENT DOCUMENTS 1092007 11/1960 Fed. Rep. of Germany.

Primary Examiner—Richard A. Schwartz
Attorney, Agent, or Firm—Norbert M. Lisicki

[57] ABSTRACT

A carbamylbiuret-modified polyisocyanate of the formula:

$$OCNR + NHC(O) - Y - C(O)NHR)_n NCO$$

wherein n is an integer of from about 1 to about 20; R is a divalent radical containing from about 1 to about 18 carbon atoms; and Y is a divalent radical selected from the group consisting of:

(a) $-N(R^2)-C(D)-N(R^3)-$ (b) five-membered ring with $R^5-C(R^4)-C(R^7)(R^6)$ and $-N-C(=X)-N-$ (c) five-membered ring with $R^5-C(R^4)-C(=X)$ and $-N-C(=X')-N-$ (d) five-membered ring with $C(=X)$, $X'=C$, $C=X''$ and two N (e) six-membered ring with $R^5-C(R^4)-C(=X)-N-$, $X'=C$, $C=X''$, N (f) six-membered ring with $X=C$, N, $C-R^4$, $C-R^5$, N, $C=X'$, and (g) six-membered ring with $O=C$, N, $C=O$, $R^4-C$, $C-H$, N wherein D is selected from the group consisting of O, S, and NH; X, X', and X" are independently selected from the group consisting of oxygen and sulfur; $R^2$ and $R^3$ are independently selected from the group consisting of aryl of from about 6 to about 18 carbon atoms, alkyl containing from about 1 to about 6 carbon atoms, and cycloalkyl containing from about 3 to about 7 carbon atoms, provided that each of $R^2$ and $R^3$ differs from R; and $R^4$, $R^5$, $R^6$, and $R^7$ are independently selected from the group consisting of hydrogen, alkyl containing from about 1 to about 6 carbon atoms, cycloalkyl containing from about 3 to about 7 carbon atoms, phenyl, and benzyl. The compounds of this invention are useful for preparing urethane-based microcellular foams and elastomers.

6 Claims, No Drawings

CARBAMYLBIURET-MODIFIED POLYISOCYANATES

This is a continuation-in-part of application Ser. No. 92479, filed Nov. 8, 1979, now U.S. Pat. No. 4,271,087.

BACKGROUND OF THE INVENTION

1. Field of the Invention

This invention relates to novel, carbamylbiuret-modified polyisocyanates which are useful for preparing urethane-based microcellular foams and elastomers having excellent physical properties.

2. Description of the Prior Art

Urethane-based microcellular foams and elastomers are widely used in industry. Thus, these foams and elastomers are used to prepare exterior automobile parts, coatings, and adhesives.

Many biuret polyisocyanates are known to those skilled in the art. These biuret polyisocyanates may be prepared by reacting an organic diisocyanate with water (U.S. Pat. Nos. 3,124,605 and 3,903,127), formic acid (U.S. Pat. No. 3,350,438), tertiary alcohols (U.S. Pat. No. 3,358,010), monoamines (U.S. Pat. No. 3,392,183), diamines (U.S. Pat. Nos. 3,441,588 and 3,903,126), ureas (U.S. Pat. No. 3,367,956 and U.K. Pat. No. 1,043,674), and other biuretizing agents (U.S. Pat. No. 3,903,127).

Biuret polyisocyanates react with compounds bearing active hydrogen to form polyurethanes; see, e.g., U.S. Pat. No. 3,201,372.

German Pat. No. 883,504 discloses a reaction between ureas and isocyanates to prepare a reaction mixture having a high isocyanate content. According to U.S. Pat. No. 3,367,956, the process of the German Patent results only in a high molecular weight condensation product.

Ureas are disclosed to react with diisocyanates by Angewandte Chemie 72 (1960), page 1002.

U.S. Pat. No. 3,367,956 discloses a process for the preparation of biuret polyisocyanates wherein an organic polyisocyanate is reacted with a substituted urea at a temperature of from about 150 to about 250 degrees Centigrade. It is believed that the process of this patent proceeds in accordance with the following reaction:

$$3OCNRNCO + R'NHCNHR' \xrightarrow{\Delta} (OCNRHC)_2NRNCO + 2R'NCO$$

(where the urea bears a C=O)

German Offen. No. 2,329,300 discloses a process for the preparation of iminoimidazolidinedions-modified polyisocyanate wherein diisocyanate is reacted with hydrocyanic acid and an organic tertiary amine catalyst.

U.S. Pat. No. 3,775,427 discloses a process for the preparation of polyisocyanates which contain hydantoin groups wherein a polyisocyanate is reacted with a α,ω-bis(hydantoinyl)alkane. The products of this patent are either viscous liquids or solids. They are unsuitable for use in urethane elastomeric microcellular foams for several reasons. In the first place, their structure contains a relatively long, flexible alkyl (or other type) bridge connecting the two hydantoin rings, thereby causing a less effective phase separation of hard and soft segments in the resulting final product and resulting in an impairment of the physical properties of the elastomer made from this product. In the second place, the physical states of these compounds and their low -NCO contents render their use in microcellular systems impractical.

SUMMARY OF THE INVENTION

This invention provides novel carbamylbiuret-modified polyisocyanates and polyurethane derived therefrom.

DETAILED DESCRIPTION OF THE INVENTION

In accordance with this invention, there is provided a carbamylbiuret-modified polyisocyanate of the formula:

$$OCNR(NHC(O)-Y-C(O)NHR)_n NCO$$

wherein n is an integer of from about 1 to about 20; R is a divalent radical containing from about 1 to about 18 carbon atoms; and Y is a divalent radical selected from the group consisting of:

(a) $-N(R^2)-C(D)-N(R^3)-$, (b) a ring: $R^5-C(R^4)-C(R^6)(R^7)$ with $-N-C(X)-N-$ closure, (c) a ring: $R^5-C(R^4)-C(X)$ with $-N-C(X')-N-$ closure, (d) a ring: $X=C$ to $N$, $X'=C$ to $N$, $C=X''$, with central N, (e) a ring with $R^4, R^5, C=X$, $X'=C$, $C=X''$, and two N's, (f) a ring: $X=C-N-C-R^4$, $-N-C(X')-C-R^5$, and

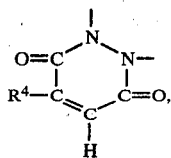

wherein D is selected from the group consisting of O, S, and NH; X, X', and X" are independently selected from the group consisting of oxygen and sulfur; $R^2$ and $R^3$ are independently selected from the group consisting of aryl of from about 6 to about 18 carbon atoms, alkyl containing from about 1 to about 6 carbon atoms, and cycloalkyl containing from about 3 to about 7 carbon atoms, provided that each of $R^2$ and $R^3$ differs from R; and $R^4$, $R^5$, $R^6$, and $R^7$ are independently selected from the group consisting of hydrogen, alkyl containing from about 1 to about 6 carbon atoms, cycloalkyl containing from about 3 to about 7 carbon atoms, and aryl of from about 6 to 18 carbon atoms.

The carbamylbiuret-modified polyisocyanates of this invention may be represented by the formula:

wherein n, R, and Y are as hereinbefore described.

It is preferred that n be from about 1 to about 20. In a more preferred embodiment, n is from about 1 to about 10.

R is an organic radical obtained by removing the —NCO groups from the organic diisocyanate used to make the carbamylbiuret-modified polyisocyanate of this invention. It is preferred that R contain from about 1 to about 18 carbon atoms. In a more preferred embodiment, R is an aromatic radical containing from about 6 to about 15 carbon atoms.

In one preferred embodiment, the carbamylbiuret-modified polyisocyanate of this invention contains carbodiimide linkages of the formula:

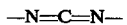

This carbodiimide-carbamylbiuret-modified polyisocyanate is prepared by reacting a carbodiimide-modified organic isocyanate with a urea-type compound. The carbodiimide-containing species in said carbodiimide-carbamylbiuret-modified polyisocyanate represent from about 2 to about 50 percent of the weight of the polyisocyanate. It is preferred that said polyisocyanate contain from about 5 to about 30 percent (by weight) of these carbodiimide species; it is even more preferred that the polyisocyanate contain from about 8 to about 20 percent (by weight) of carbodiimide species.

Any suitable carbodiimide-modified organic polyisocyanate may be used to prepare the carbodiimide-carbamylbiuret-modified polyisocyanate of this invention. These carbodiimide-modified organic polyisocyanates are well known to those skilled in the art. They may be prepared, e.g., by the procedures described in U.S. Pat. No. 3,152,162, in German Pat. No. 1,092,007, in an article by T. W. Campbell and K. C. Smeltz appearing in *J. Org. Chem.*, 28, 2069 (1963), and in an article by D. J. Lyman and N. Sadri appearing in *Makromel. Chem.*, 67, 1 (1963).

One means of preparing the carbodiimide-modified polyisocyanates used in the process of this invention is to heat the organic diisocyanates known to the art. Extended heating of isocyanates results in the condensation of the isocyanate to a carbodiimide with elimination of carbon dioxide in accordance with the following equation:

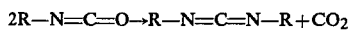

Certain phospholenes and phospholene oxides catalyze the transformation of isocyanates to carbodiimide linkages, e.g., 1-ethyl-3-methyl-3-phospholene oxide, 1-phenyl-3-methyl-3-phospholene oxide. Also, simple trialkyl phosphine oxides, and the like may be used to catalyze the reaction.

The carbodiimide-modified polyisocyanates which are used to prepare the carbodiimide-carbamylbiuret-modified polyisocyanates of this invention have NCO contents of from about 20 to about 31 percent and contain from about 5 to about 50 percent (by weight) of carbodiimide-containing species. It is preferred that said carbodiimide-modified polyisocyanates have NCO contents of from about 26 to about 30 percent and contain from about 10 to about 35 percent (by weight) of carbodiimide-species. In the most preferred embodiment, the carbodiimide-modified polyisocyanates have NCO contents of from about 28 to about 30 percent and contain from about 15 to about 25 percent (by weight) of carbodiimide-species.

In one preferred embodiment, the carbodiimide-modified polyisocyanate is prepared by heating to a temperature of from about 150 to about 300 degrees Centigrade a polyisocyanate of the diphenyl methane series until a maximum of 33 percent of the existing isocyanate groups have reacted to form the carbodiimide. This carbodiimide-modified polyisocyanate is prepared in accordance with the procedure of U.S. Pat. No. 3,152,162. One of its most preferred embodiments absorbs light in the infrared range of from 5.76 to 5.78 microns and from 7.22 to 7.24 microns.

In another preferred embodiment, R is

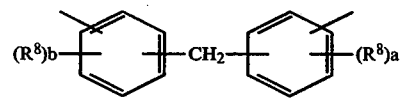

where $R^8$ is methyl and a and b are integers of from 0 to 2. In this embodiment it is preferred that R be

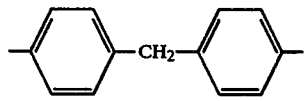

It is preferred that the carbamylbiuret-modified polyisocyanate of this invention have an NCO content of from about 20 to about 32 percent. It is more preferred that the NCO content of this polyisocyanate be from about 22 to about 31 percent.

Y is a divalent radical derived from the urea-type compounds which are used to prepare the polyisocyanates of this invention. In general, Y is obtained by removing hydrogen atoms from the nitrogen atoms in the urea-type compound.

The preferred urea-type compounds which may be used to prepare the compositions of this invention are described by the formulae:

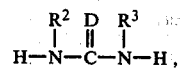 (a)

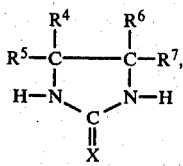 (b)

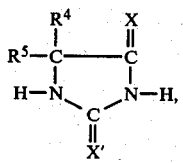 (c)

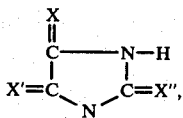 (d)

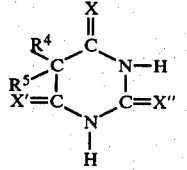 (e)

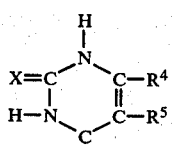 (f)

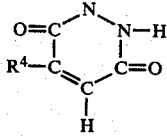 (g)

wherein $R^2$, $R^3$, $R^4$, $R^5$, $R^6$, $R^7$, X, X', and X" are as hereinbefore described. By way of illustration and not limitation, some of the preferred ureas which may be used to prepare the compositions of this invention include N,N'-dimethylurea, N,N'-dimethylthiourea, N,N'-diethylurea, N,N'-diethylthiourea, N,N'-di-n-propylurea, N,N'-di-n-propylthiourea, N,N'-di-t-butylurea, N,N'-di-t-butylthiourea, N,N'-dicyclohexylurea, N,N'-dicyclohexylthiourea, N,N'-diphenylurea, N,N'-diphenylthiourea, N-methyl-N'-benzylurea, N-methyl-N'-benzylthiourea, ethyleneurea, ethylenethiourea, propyleneurea, propylenethiourea, n-butyleneurea, n-butylenethiourea, hydantoin, 5-methylhydantoin, 5-ethylhydantoin, 5-n-propylhydantoin, 5-t-butylhydantoin, 5-nitrohydantoin, 5-sec-butylhydantoin, 5-phenylhydantoin, 2-thiohydantoin, 4-thiohydantoin, 2,4-dithiohydantoin, 5,5-dimethylhydantoin, 5,5-diethylhydantoin, 5,5-di-n-propylhydantoin, 5,5-diphenylhydantoin, 5-methyl-5-ethylhydantoin, 5-methyl-5-isopropylhydantoin, 5,5-diphenyl-2-thiohydantoin, 1,3-diphenylguanidine, allantoin, barbituric acid, parabanic acid, cyanuric acid, uracil, and the like.

Any suitable organic isocyanate may be used in the process of this invention. One may use isocyanates which contain substantially no carbodiimide linkages in said process; when this is done, one obtains carbamylbiuret-modified polyisocyantes. Alternatively, one may convert an isocyanate to carbodiimide linkages by heat or catalyst and then react the product obtained with the urea-type compounds; when this is done, one obtains carbodiimide-carbamylbiuret-modified polyisocyanates. Thus, some of the isocyanates which may be used in this process include, for example, aromatic isocyanates such as, 1-methylbenzene-2,4-diisocyanate, 1-methylbenzene-2,6-diisocyanate, 1-methoxybenzene-2,4-diisocyanate, 1-chlorobenzene-2,4-diisocyanate, 1-benzylbenzene-2,6-diisocyanate, 2,6-diethylbenzene-1,4-diisocyanate, diisopropylbenzene diisocyanates, triisopropylbenzene diisocyanates, 1,3-dimethoxybenzene-2,4-diisocyanate, 1-nitrobenzene-2,4-diisocyanate, technical mixtures of 2,4- and 2,6-toluene diisocyanates, m- and p-phenylene diisocyanates, m-xylylene diisocyanate, p-xylylene diisocyanate, naphthylene-1,5-diisocyanate, diphenylmethane-4,4'-diisocyanate, diphenylmethane-2,2'-diisocyanate, diphenylmethane-4,2'-diisocyanate, 3,3'-dimethoxydiphenylmethane-4,4'-diisocyanate, dimethyldiphenylmethane-4,4'-diisocyanate, 3-methyldiphenylmethane-4,4'-diisocyanate, 1-(isocyanatophenyl)-ethyl isocyanate, 4,4'-biphenyl diisocyanate, 4,4'-diphenyl sulphone diisocyanate, aromatic diisocyanates which have been substituted by various substituents such as alkoxy-, nitro, chloro, or bromo-, chlorophenylene-2,4-diisocyanate, and the like. Thus, one may use aliphatic, cycloaliphatic, and araliphatic isocyanates such as, tetramethylene diisocyanate, pentamethylene diisocyanate, hexamethylene diisocyanate, 1,3-cyclopentylene diisocyanate, 1,4-cyclohexylene diisocyanate, 1,2-cyclohexylene diisocyanate, hexahydroxylylene diisocyanate, 4,4'-dicyclohexyl diisocyanate, 1,2-di-(isocyanatomethyl)-cyclobutane, 1,3-bis-(isocyanatopropoxy)-2,2-dimethyl propane, 1,3-bis-(isocyanato-propyl)-2-methyl-2-propylpropane, 1-methyl-2,4-diisocyanatocyclohexane, 1-methyl-2,6-diisocyanatocyclohexane, bis-(4-isocyanatocyclohexyl)-methane, 1,4-diisocyanatocyclohexane, 1,3-diisocyanatocyclohexane, isophorone diisocyanate, 2,6-diisocyanatocaproic acid ester, an isomeric mixture of 1-methyl-2,4-diisocyanatocyclohexane and 1-methyl-2,6-diisocyanatocyclohexane, 3,3,5-trimethyl-5-isocyanatomethylcyclohexylisocyanate, methyl-substituted hexamethylene- and pentamethylene-diisocyanate, and the like. Other organic isocyanates well known to those in the art also may be used such as, mixtures of 2,2'-, 2,4'-, and 4,4'-diphenylmethane diisocyanates, polyphenylpolymethylenepolyisocyanates, mixtures of diphenylmethane diisocyanates and polyphenylpolymethylenepolyisocyanates, mixtures of 4,4'-diphenylmethane diisocyanates and 2,4- and 2,6-toluene diisocyanates, crude isocyanates from the phosgenation of toluene diamine, and the like.

It is preferred to use a diisocyanate selected from the group consisting of toluene diisocyanate, hexamethylene diisocyanate, diphenylmethane diisocyanate, and the dimethyl derivative of diphenylmethane diisocyanate. The most preferred diisocyanate is diphenylmethane diisocyanate.

The compositions of this invention may be prepared by reacting an isocyanate of the formula OCNRNCO (reactant I) with a urea-type compound of the formula HYH (reactant II). From about 2 to about 50 moles of reactant I are used for each mole of reactant II. It is preferred to use a reactant I/reactant II mole ratio of from about 3 to about 25; in the most preferred embodiment, said mole ratio is from about 5 to about 20.

In the process of this invention, reactants I and II are heated together at a temperature of from about 60 to about 250 degrees Centigrade for from about 0.2 to about 20 hours until the NCO content of the reaction mixture is from about 20 to about 32 percent. It is preferred to heat reactants I and II at a temperature of from about 80 to about 250 degrees Centigrade for from about 0.2 to about 15 hours until the NCO content of the reaction mixture is from about 22 to about 31 percent. In the most preferred embodiment, the reactants are heated at a temperature of from about 80 to about 230 degrees Centigrade for from about 0.2 to about 10 hours until the NCO content of the reaction mixture is from about 22 to about 30 percent.

It is preferred to use nitrogen as a blanketing gas in the process of this invention.

The reaction between reactants I and II may be carried out with or without a solvent. If a solvent is used, it is preferred that it not contain any hydrogen atoms which would react with —NCO groups. Suitable solvents include ethyl acetate; ketones, glycolmethyl ether acetate; chlorinated aliphatic, hydroaromatic, or aromatic hydrocarbons such as methylene chloride, perchlorocyclohexane, orthodichlorobenzene; and the like.

The polyisocyanates of this invention may be used to prepare cellular polyurethanes by reacting them with an active hydrogen-containing compound in the presence of a blowing agent. A suitable apparatus and process which may be used to prepare cellular polyurethane plastics are described in U.S. Pat. No. Re. 24,514.

Water may be added as the blowing agent. When water is used, corresponding quantities of excess isocyanate which react with the water and produce carbon dioxide may be used.

One may also prepare the polyurethane plastics of this invention be a prepolymer technique wherein an excess of organic polyisocyanate is reacted in a first step with a polyol to prepare a prepolymer having free —NCO groups and the prepolymer is reacted in a second step with polyol and a blowing agent to prepare a foam. When this is done, water or low-boiling hydrocarbons may be used as the blowing agents. Some hydrocarbons which are suitable for this purpose include pentane; hexane; heptane; pentene; heptene; halogenated hydrocarbons such as, dichlorodifluoroethane, dichlorodifluoromethane, trichlorofluoromethane, vinylidene chloride, methylene chloride, mixtures of the aforementioned, and the like; azo compounds such as azohexahydrobenzodinitrile; and other blowing agents well known to those in the art.

Alternatively, one may react the polyisocyanate of this invention and the active hydrogen-containing compound in a single step. When this is done, it is preferred that one use a suitable catalyst such as, stannous chloride, a stannous salt of a carboxylic acid having from 1 to 18 crbon atoms, a trialkyl tin oxide, a dialkyl tin chloride, a dialkyl tin oxide or a dialkyl tin salt of a carboxylic acid having from about 1 to about 18 carbon atoms, and other catalysts well known to those skilled in the art for this purpose. The aforementioned catalysts may be used by themselves or in combination with another suitable catalytic compound such as, a tertiary amine (such as triethylenediamine); N,N,N',N'-tetramethyl butanediamine; a 1-alkyl-4(dialkylaminoalkyl) piperazine in which the alkyl radicals of the dialkylamino group contain from about 1 to about 4 carbon atoms and the alkyl radical bearing the dialkylamino group contains from about 2 to about 4 carbon atoms; N-ethylmorpholine; the catalysts disclosed in U.S. Pat. Nos. 2,948,928, 2,941,967, 2,948,691; and other catalysts well known to those in the art.

The polyisocyanate of this invention is reacted with an organic compound which contains active hydrogen-containing groups. By way of illustration and not limitation, some of the active hydrogen-containing compounds which may be used in the process of this invention include polyester polyols, polyether polyols, polythioether polyols, polyacetals polyols, and the like.

Any suitable organic compound which contains at least two active hydrogen-containing groups (as determined by the Zerewitinoff method) may be used in the process of this invention.

In one preferred embodiment, said organic compound contains a plurality of active hydrogen-containing groups and at least some alcoholic hydroxyl groups. The hydroxyl groups react with —NCO groups to yield urethane groups. The alcoholic group is preferred because it is readily available and yields a stronger urethane linkage than a phenolic type hydroxyl group.

The organic compound which contains at least two active hydrogen-containing groups may contain, —OH, —NH$_2$, —NH, —COOH, and —SH groups. Some examples of this type of organic compound include, polyhydroxyl polyesters; polyhydric polyalkylene ethers; polyhydric polythioethers; polyacetal polyols; aliphatic polyols such as, alkane, alkene, and alkyne diols, triols, tetrols, and the like; aliphatic thiols including alkane, alkene, and alkyne thiols having two or more —SH groups; polyamines including both aromatic, aliphatic, and heterocyclic diamines, triamines, tetramines, and the like. Compounds which contain two or more active hydrogen-containing groups also may be used in the process of this invention; thus, one may use amino alcohols which contain two amino groups and one hydroxyl group, compounds which contain one —SH group and one —OH group, compounds which contain two —OH groups and one —SH group, compounds which contain an amino group and an —SH group, and the like.

The molecular weight of the organic compound containing the active hydrogen-containing groups may vary over a wide range. It is preferred that at least one of the active hydrogen-containing compounds have a molecular weight of at least about 200. It is more preferred that said compound have a molecular weight of from about 500 to about 5000, a hydroxyl number of from about 25 to about 800, and an acid number (where applicable) of below about 5. It is preferred that the molecular weight of said compound not exceed about 10,000, but a higher molecular weight can be used as long as satisfactory mixing of the active hydrogen-containing compound with the polyisocyanate of this invention can be obtained.

In one preferred embodiment, an organic compound containing active hydrogen groups with a molecular weight of from about 200 to about 10,000 is used together with an organic compound with active hydrogen-containing groups which has a molecular weight of below about 750. It is preferred that the molecular weight of this latter compound be below about 500. Aliphatic diols and triols are most preferred for this purpose.

The active hydrogen-containing organic compound may be a polyhydroxyl polyester. Any suitable hydroxyl polyester may be used such as those obtained from polycarboxylic acids and polyhydric alcohols.

The active hydrogen-containing compound may be a polycarboxylic acid. Any suitable polycarboxylic acid may be used such as, oxalic acid, malonic acid, succinic acid, glutaric acid, adipic acid, pimelic acid, suberic acid, azelaic acid, brassylic acid, sebacic acid, thapsic acid, maleic acid, fumaric acid, glutaconic acid, alpha-hydromuconic acid, beta-hydromuconic acid, alpha-butyl-alpha-ethylglutaric acid, alpha, beta-diethylsuccinic acid, isophthalic acid, terephthalic acid, hemimellitic acid, trimellitic acid, trimesic acid, mellophanic acid, prehnitic acid, pyromellitic acid, benzenepentacarboxylic acid, 1,4-cyclohexanedicarboxylic acid, 3,4,9,10-perylenetetracarboxylic acid, and the like.

The active hydrogen-containing compound may be a polyhydric alcohol such as; ethylene glycol, propylene glycol, 1,3-propane diol, butylene glycol, 1,4-butane diol, 1,3-butane diol, 1,5-pentane diol, 1,4-pentane diol, 1,3-pentane diol, 1,6-hexane diol, 1,7-heptane diol, glycerine, trimethylolpropane, 1,3,6-hexanetriol, triethanolamine, pentaerythritol, sorbitol, and the like.

The active hydrogen-containing compound may be a polyhydric polyalkylene ether. Some suitable polyhydric polyalkylene ethers include, for example, the condensation product of an alkylene oxide wherein the condensation is initiated with compounds known to the art. The initiator may be a difunctional compound, such as water, so that the resulting polyether is essentially a chain of repeating oxyalkylene groups as one finds in polyethylene ether glycol, polypropylene ether glycol, polybutylene ether glycol, and the like. The initiator may be any suitable active hydrogen-containing compound. It is preferred that the initiator contain from about 2 to about 8 active sites to which the alkylene oxides may add. Alkylene oxides which may be used to prepare the polyhydric polyalkylene ether include ethylene oxide, propylene oxide, butylene oxide, amylene oxide, epihalohydrins such as, epichlorohydrin, styrene oxide, and the like. Initiators which may be used include water, ethylene glycol, propylene glycol, glycerine, trimethylolpropane, pentaerythritol, sorbitol, sucrose, ammonia, diethanolamine, triethanolamine, dipropanolamine, tripropanolamine, 2,4-tolylenediamine, 4,4'-diphenylmethanediamine, p, p', p"-triphenylmethanetriamine, ethylenediamine, propylenediamine, dipropylenetriamine, N,N,N',N'-tetrakis-(2-hydroxypropyl) ethylenediamine, diethylenetriamine, and the like.

The process for preparing polyhydric polyalkylene ethers is well known to those in the art and is described in U.S. Pat. Nos. 1,922,459, 3,009,939, and 3,061,625 and in the Encyclopedia of Chemical Technology, Volume 7, pages 257 to 262, published by Interscience Publishers, Inc., in 1951.

The active hydrogen-containing compound may be a polyhydric polythioether. Some of the polyhydric polythioethers which may be used in the process of this invention include the condensation product of thiodiglycol, the reaction product of a polyhydric alcohol with a thioetherglycol, and the polyhydric polythioethers disclosed in U.S. Pat. Nos. 2,862,972 and 2,900,368.

A polyhydroxyl polyester which is also a polyester amide also may be used as the active hydrogen-containing compound. Thus, such compounds may be prepared by including some amine or amino alcohol in the reactants used for the preparation of the polyhydroxyl polyesters. Polyester amides may be obtained by condensing an amino alcohol (such as ethanolamine) with the polycarboxylic acids described hereinabove; or they may be made with the same components used for the polyhydroxyl polyester with a portion of the components being a diamine.

The active hydrogen-containing compound may be a polyacetal polyol. Some suitable polyacetals include, the reaction product of an aldehyde (such as formaldehyde) with a polyhydric alcohol.

In one preferred embodiment, the active hydrogen-containing compound is an aliphatic polyol. Some of the suitable aliphatic polyols which may be used include, alkanediols such as, ethylene glycol, trimethylene glycol, propylene glycol, tetramethylene glycol, 1,3-butanediol, 1,5-pentanediol, 1,3-pentanediol, 1,6-hexanediol, 1,7-heptanediol, 2,2-dimethyl-1,3-propanediol, 1,8-octanediol, 1,20-eicosanediol, and the like; alkenediols such as, 2-pentene-1,5-diol, 2-hexene-1,6-diol, 2-hexene-1,7-diol, and the like; alkyne diols such as, 2-butyne-1,4-diol, and the like; alkanetriols such as, 1,3,6-hexanetriol, 1,3,7-heptanetriol, 1,4,8-octanetriol, 1,6,12-dodecanetriol, and the like; alkenetriols such as, alkynetriols such as 2-hexyne-1,3-6-triol and the like; alkanetetrols such as, 1,2,5,6-hexanetetrol; alkenetetrols such as, 3-heptene-1,2,6,7-tetrol; alkynetetrols such as, 4-octyne-1,2,7,8-tetrol; and other aliphatic polyols well known to those skilled in the art.

The active hydrogen-containing compound may be an aliphatic thiol which contains two or more -SH groups. Some suitable aliphatic thiols include, 1,2-ethanedithiol, 1,3-propanedithiol, 1,2-propanedithiol, 1,6-hexanedithiol, 1,3,6-hexanetrithiol, 2-butene-1,4-dithiol, 3-hexyne-1,6-dithiol, and the like.

The active hydrogen-containing compound may be a polyamine. Some suitable polyamines include, aromatic polyamines such as, p-aminoaniline, 1,5-diaminoaphthalene, 2,4-diaminotoluene, 1,3,5-benzenetriamine, 1,2,3-benzenetriamine, 1,4,5,8-naphthalenetetramine, and the like; aliphatic polyamines such as, ethylenediamine, 1,3-propanediamine, 1,4-butanediamine, 1,3-butanediamine, diethylenetriamine, triethylenetetramine, 1,3,6-hexanetriamine; 1,3,5,7-heptanetetramine, and the like.

The following examples are presented to illustrate the claimed invention and are not to be deemed limitative thereof. Unless otherwise stated, all parts are by weight, all percentages are by weight, and all temperatures are in degrees Centigrade.

EXAMPLES 1–27

The specified amounts of diphenylmethane diisocyanate (MDI) and a urea-type compound were heated under nitrogen under the time and temperature conditions described until the NCO content reached a predetermined level. In Examples 1–7 the urea-type compound was 2-imidazolidone. In Examples 8–13 the urea-type compound was 5,5-dimethylhydantoin. In Examples 14–15 the urea-type compound was hydantoin. In Examples 16–18 the urea-type compound was 1,3-dimethylurea. In Examples 19–22 the urea-type compound was 5,5-diphenylhydantoin. In Example 23, 3,6-dihydroxy pyridazine was used as the urea-type compound. 2-Imidazolidinethione and 1,3-diphenylguanidine were used as the urea-type compounds in Examples 24–25 and 26–27, respectively.

| Example | MDI, grams | Urea-Type Compound grams | Reaction Temperature, °C. | Reaction Time, hours | % NCO |
|---|---|---|---|---|---|
| 1 | 1930 | 170.0 | 120–150 | 3.0 | 22.4 |
| 2 | 1978 | 122.0 | 120–150 | 3.0 | 26.0 |
| 3 | 2044 | 56.0 | 120 | 1.0 | 30.4 |
| 4 | 2100 | 42.0 | 200 | 5.7 | 29.6 |
| 5 | 2100 | 58.0 | 200 | 0.5 | 28.5 |
| 6 | 2100 | 63.0 | 200 | 15.8 | 26.1 |
| 7 | 2100 | 130.0 | 55–200 | 0.6 | 25.7 |
| 8 | 1609 | 190.8 | 220 | 6.5 | 22.9 |
| 9 | 1663 | 136.8 | 220 | 5.3 | 26.1 |
| 10 | 1473 | 55.0 | 220 | 2.2 | 29.8 |
| 11 | 2100 | 78.4 | 220 | 4.2 | 29.2 |
| 12 | 2100 | 172.7 | 220 | 4.2 | 26.0 |
| 13 | 2100 | 268.9 | 230 | 0.7 | 26.0 |
| 14 | 2035 | 65.0 | 220 | 1.2 | 30.3 |
| 15 | 1403 | 97.5 | 220 | 2.2 | 23.7 |
| 16 | 1928 | 172.2 | 120 | 19.5 | 23.5 |
| 17 | 1976 | 123.9 | 120 | 13.0 | 26.2 |
| 18 | 2041 | 58.8 | 120 | 5.0 | 30.4 |
| 19 | 2100 | 52.5 | 230 | 9.0 | 25.7 |
| 20 | 2100 | 52.5 | 230 | 15.5 | 20.0 |
| 21 | 2100 | 119.7 | 230 | 1.2 | 30.1 |
| 22 | 2100 | 268.8 | 230 | 2.6 | 25.5 |
| 23 | 2100 | 52.5 | 200 | 1.7 | 30.7 |
| 24 | 2100 | 67.2 | 200 | 1.0 | 29.1 |
| 25 | 2100 | 147.0 | 200 | 2.0 | 24.0 |
| 26 | 2100 | 84.0 | 200 | 0.75 | 26.9 |
| 27 | 2100 | 63.0 | 67–200 | 0.7 | 28.9 |

EXAMPLE 28

In substantial accordance with the procedure described in Examples 1–27, 600 grams of a pure diphenylmethane diisocyanate (isocyanate 1) were reacted with 36 grams of diethylurea at a temperature of 100 degrees Centigrade for 2.0 hours until the NCO content of the reaction mixture was 29.2 percent. The product had a viscosity of 42 centipoises (at 25 degrees Centigrade).

EXAMPLE 29

In substantial accordance with the procedure described for Examples 1–27, 600 grams of isocyanate 1 were reacted with 36 grams of dicyclohexylurea at a temperature of 120 degrees Centigrade for 3.0 hours until the NCO content of the reaction mixture was 29.6 percent. The product had a viscosity of 42 centipoises (at 25 degrees Centigrade).

EXAMPLE 30

An isocyanate blend containing equal parts of an isocyanate derived from low molecular weight glycol and diphenylmethane diisocyanate (isocyanate 2) and of the isocyanate of Example 3 was prepared by rolling the isocyanates for 1–2 hours. Three hundred point eight (300.8) parts of this isocyanate blend were weighed into a quart Plastikan, and 400 parts of a resin blend were added rapidly to the Plastikan. The resin blend contained components in the ratio of 70 parts (by weight) of an ethylene oxide capped polyol of oxypropylated propylene glycol with a molecular weight of 3500 (polyol 1), 30 parts (by weight) of a 6700 molecular weight triol (polyol 2), 23.5 parts (by weight) of 1,4-butanediol, 0.02 parts (by weight) of dibutyltindilaurate, and 2.0 parts (by weight) of a solution containing a 1:3 mixture (by weight) of triethylene diamine and 1,4-butanediol.

The mixture of the isocyanate blend and the resin blend were agitated in the Plastikan with a high-speed drill fitted with a Cowles dissolver for 10 seconds. The system blend was poured quickly into an all-aluminum mold preheated to a temperature of 130–140 degrees Fahrenheit. After 4 minutes, the resulting solid pad was pulled from the mold and post-cured in an oven for one hour at a temperature of 250 degrees Fahrenheit. The solid pad was then aged for from about 3 to 5 days at room temperature and thereafter evaluated.

Physical tests were performed in accordance with procedures well known to those skilled in the art. The density determinations were made in accordance with the procedure described in A.S.T.M. D-792. The tensile strength, tensile modulus, and elongation determinations were made in accordance with the procedure described in A.S.T.M. D-412. The split tear test is described in A.S.T.M. D-1938. The Shore D hardness procedure is described in A.S.T.M. D-2240. The flex modulus test was conducted in accordance with A.S.T.M. D-790. The flex recovery test is described in Materials Standard #CTZ 22003, Chevrolet Motor Standard, G.M.C. The heat sag determination was done in accordance with Materials Standard #CTZ 22006, Chevrolet Motor Division, G.M.C. The Dart impact test is described in Fisher Body Specification FBMS 2-23. Each of these publications is hereby incorporated into this specification by reference.

The polyurethane foam of this Example had a density (pcf.) of 61.96; a tensile-strength (p.s.i.) of 2010; a tensile modulus (p.s.i., 100%) of 1655; an elongation (percent) of 220; a split tear (pounds per inch) of 416; a Graves tear (Die C, pounds per inch) of 508; a Shore D hardness of 55-50; a flex recovery of 14.5/7; a flex modulus (in thousands of pounds per square inch) of 74.07, 26.5, and 10.91 at minus 20 degrees Fahrenheit, 72 degrees Fahrenheit, and 150 degrees Fahrenheit, respectively; a heat sag (at 250 degrees Fahrenheit) of 0.28; and Dart impact rating of NF, NF, and F at 20 degrees Fahrenheit, 10 degrees Fahrenheit, and 0 degrees Fahrenheit, respectively.

COMPARATIVE EXAMPLE 31

In substantial accordance with the procedure of Example 30, a polyurethane foam was prepared using an isocyanate blend containing 50 parts of isocyanate 2 and 50 parts of a carbodiimide-modified polyisocyanate (isocyanate 3), the carbamylbiuret-modified polyisocyanate of this invention was not used in the experiment described in this Example.

The polyurethane foam of this Example had a density (pcf.) of 61.43; a tensile strength (p.s.i.) of 1940; a tensile modulus (p.s.i., 100%) of 1800; an elongation (percent) of 115; a split tear (pounds per inch) of 175; A Graves tear (Die C, pounds per inch) of 424; a Shore D hardness of 53-51; a flex recovery of 14/8; a flex modulus (pounds per square inch $\times 10^3$) of 65.88, 30.99, and 14.54 at minus 20 degrees Fahrenheit, 72 degrees Fahrenheit, and 150 degrees Fahrenheit, respectively; a heat sag (at 250 degrees Fahrenheit) of 0.13; and Dart impart ratings of NF, NF, and F at 20 degrees Fahrenheit, 10 degrees Fahrenheit, and 0 degrees Fahrenheit, respectively.

Several of the properties of the polyurethane foam of Example 30 were substantially superior to the properties of the foam of Example 31. It appears that the use of the carbamylbiuret-modified polyisocyanate of this invention improved the elongation, split tear, and Graves tear properties.

COMPARATIVE EXAMPLE 32

In substantial accordance with the procedure of Example 30, a polyurethane foam was prepared using 100 parts of isocyanate 2; no other isocyanate was used in this experiment.

The polyurethane foam of this Example had a density (pcf.) of 61.07; a tensile strength (p.s.i.) of 1970; a tensile modulus (p.s.i., 100%) of 1675; an elongation (percent) of 195; a split tear (pounds per inch) of 344; a Graves tear (Die C, pounds per inch) of 508; a Shore D hardness of 54-48; a flex recovery of 16/8; a flex modulus (pounds per square inch $\times 10^3$) of 107.11, 27.82, and 7.52 at 20 degrees Fahrenheit, 72 degrees Fahrenheit, and 150 degrees Fahrenheit, respectively; a heat sag (at 250 degrees Fahrenheit) of 0.55; and Dart impact ratings of NF/F, NF/F, and F at 20 degrees Fahrenheit, 10 degrees Fahrenheit, and 0 degrees Fahrenheit, respectively.

The elongation and split tear properties of the polyurethane foam of Example 30 was substantially superior to the elongation and split tear properties of the polyurethane foam of this Example.

EXAMPLES 33 AND 34

In substantial accordance with the procedure of Example 30, a polyurethane foam was prepared from an isocyanate blend containing 75 parts of isocyanate 3 and 25 parts of the isocyanate of Example 9.

In substantial accordance with the procedure of Example 30, a polyurethane foam was prepared from an isocyanate blend containing 75 parts of isocyanate 3 and 25 parts of isocyanate 2.

The properties of each of these foams were determined; these properties are shown below.

|  | Foam Produced from Blend Containing 25 Parts of the Isocyanate of Example 9 | Foam Produced from Blend Containing 25 Parts of Isocyanate 2 |
|---|---|---|
| Density (pcf.) | 63 | 61 |
| Tensile strength (p.s.i.) | 2280 | 2015 |
| Tensile modulus (p.s.i., 100%) | 1935 | 1860 |
| Elongation (percent) | 180 | 135 |
| Split tear (p.i.) | 225 | 171 |
| Graves tear (Die C, p.i.) | 439 | 412 |
| Shore D hardness | 54-52 | 54-56 |
| Flex recovery | 10/5 | 13/7 |
| Heat sag @ 250° C. | 0.21 | 0.12 |
| Flex modulus (p.s.i. $\times 10^3$) |  |  |
| −20° F. | 57.27 | 54.71 |
| 72° F. | 27.1 | 25.6 |
| 150° F. | 13.79 | 13.70 |
| Dart impact at |  |  |
| 20° F. | NF | NF |
| 10° F. | NF | NF |
| 0° F. | F | F |

It appears that the use of the carbamylbiuret-modified isocyanate of this invention improve the elongation, split tear, and Graves tear properties of the polyurethane foam.

EXAMPLES 35 AND 36

In substantial accordance with the procedure of Example 30, a polyurethane foam was prepared from an isocyanate blend containing 75 parts of isocyanate 2 and 25 parts of the isocyanate of Example 10.

In substantial accordance with the procedure of Example 30, a polyurethane foam was prepared from an isocyanate blend containing 75 parts of isocyanate 2 and 25 parts of isocyanate 3.

The properties of each of these foams were determined; these properties are shown below.

|  | Foam Produced from Blend Containing 25 Parts of the Isocyanate of Example 10 | Foam Produced from Blend Containing 25 Parts of Isocyanate 3 |
|---|---|---|
| Density (pcf.) | 62 | 61 |
| Tensile strength (p.s.i.) | 2150 | 2155 |
| Tensile modulus (p.s.i., 100%) | 1805 | 1845 |
| Elongation (percent) | 245 | 185 |
| Split tear (p.i.) | 241 | 225 |
| Graves tear (die C, p.i.) | 582 | 463 |
| Shore D hardness | 52-49 | 55-52 |
| Flex recovery | 15/8.5 | 12/8 |
| Heat sag @ 250° C. | 0.18 | 0.25 |
| Flex modulus (p.s.i. $\times 10^3$) |  |  |
| −20° F. | 72.74 | 79.67 |
| 72° F. | 22.77 | 29.12 |
| 150° F. | 13.43 | 13.43 |
| Dart impact at |  |  |
| 20° F. | NF | NF |
| 10° F. | NF/F | NF/F |
| 0° F. | F | F |

The use of the isocyanate of this invention substantially improved the elongation and Graves tear properties of the polyurethane foam.

EXAMPLES 37-41

In substantial accordance with the procedure of Example 30, polyurethane foams were prepared from various isocyanate blends. In Example 37 the blend contained 50 parts of isocyanate 3 and 50 parts of the isocyanate of Example 3. In Example 38 the blend contained 75 parts of isocyanate 3 and 25 parts of the isocyanate of Example 15. In Example 39 the blend contained 50 parts of isocyanate 2 and 50 parts of the isocyanate of Example 15. In Example 40 the blend contained 75 parts of isocyanate 3 and 25 parts of the isocyanate of Example 16. In Example 41 the blend contained 75 parts of isocyanate 2 and 25 parts of the isocyanate of Example 16.

The properties of each of these foams were determined and are shown below.

|  | 37 | 38 | 39 | 40 | 41 |
|---|---|---|---|---|---|
| Density (pcf) | 63 | 63 | 66 | 63 | 61 |
| Tensile strength (p.s.i.) | 1950 | 2065 | 1733 | 2090 | 2120 |
| Tensile modulus, p.s.i., 100% | 1820 | 1855 | 1633 | 1850 | 1770 |
| Elongation, Percent | 115 | 155 | 183 | 145 | 265 |
| Split tear, p.i. | 130 | 211 | 307 | 212 | 475 |
| Graves tear, Die C, p.i. | 344 | 388 | 440 | 425 | 500 |
| Shore D hardness | 50-43 | 53-52 | 57-51 | 54-51 | 56-52 |
| Flex recovery | 9/5.5 | 12.58 | 18/11 | 11/6.5 | 16.8.5 |
| Heat sag @ 250° F. | 0.25 | 0.20 | 0.43 | 0.18 | 0.28 |
| Flex modulus p.s.i. $\times 10^3$ |  |  |  |  |  |
| −20° F. | 41.36 | 61.93 | 84.59 | 56.56 | 76.66 |
| 72° F. | 17.89 | 27.77 | 28.68 | 26.58 | 28.0 |
| 150° F. | 11.84 | 13.43 | 14.53 | 12.78 | 11.37 |
| Dart impact at |  |  |  |  |  |
| 20° F. | NF | NF | F | NF | NF |

-continued

|      | 37 | 38   | 39 | 40 | 41   |
|------|----|------|----|----|------|
| 10° F. | NF | NF/F | —  | NF | NF/F |
| 0° F.  | NF | F    | F  | F  | F    |

When the procedure of Example 30 is repeated with the exception that a different isocyanate blend is used, similarly good results are obtained. Carbamylbiuret-modified polyisocyanates are prepared with the following organic diisocyanates and urea-type compounds in substantial accordance with the procedure described in Examples 1–27. Each of the organic diisocyanates selected from the group consisting of 4,4-dephenylmethane diisocyanate, p-phenylene diisocyanate, p-xylylene diisocyanate, and 4,4′-biphenyl diisocyanate is reacted with each of the urea compounds selected from the group consisting of N,N-diethylurea, N,N-dipropylurea, N,N-di-n-propylurea, N,N-dicyclohexylurea, 5-ethylhydantoin, 5,5-diethyldantoin, and 1,3-diphenylguanidine. When these polyisocyanates are used to prepare microcellular polyurethane foams, good results are obtained.

The carbamylbiuret-modified polyisocyanate of this invention is more linear and symmetrical than prior art products; and it can be used to prepare elastomeric products with physical properties which are superior to prior art elastomers. These novel carbamylbiuret-modified polyisocyanates are capable of forming hydrogen bonds; it is believed that, for elastomer applications, this capability enables these novel polyisocyanates to form hydrogen bonds and to increase strength properties and ring-pseudo-ring packing of the type which will constitute a hard phase, thereby improving the properties of the elastomer.

EXAMPLES 42–46

The specified amounts of isocyanate 3 and a urea-type compound were heated under the time and temperature conditions described until the NCO content reached a predetermined level. In Examples 42, 43, and 44 the urea-type compound was 1,3-dimethylurea; in Examples 45 and 46 the urea-type compound was 5,5-dimethylhydantoin.

| Example | Parts of Isocyanate 3 (by weight) | Parts of Urea-Type Compound (by weight) | Reaction Temperature, °C. | Reaction Time, hours | % NCO | Viscosity CPS/°C. |
|---------|-----------------------------------|-----------------------------------------|---------------------------|----------------------|-------|-------------------|
| 42 | 100 | 3 | 100 | 0.5 | 26.1 | 100/26 |
| 43 | 100 | 6 | 100 | 7.5 | 23.7 | 380/28 |
| 44 | 100 | 4 | 80  | 0.5 | 25.5 | 141/27 |
| 45 | 100 | 3 | 100 | 5.0 | 26.6 | 150/26 |
| 46 | 100 | 3 | 200 | 1.0 | 25.7 | 450/26 |

EXAMPLES 47–52

In substantial accordance with the procedure described for Examples 42–46, an isocyanate blend containing 50 parts (by weight) of isocyanate 3 and 50 parts (by weight) of isocyanate 1 were heated with the specified amounts of a urea-type compound under the time and temperature conditions described until the NCO content reached a predetermined level. In Examples 47, 48, and 49 the urea-type compound was 1,3-dimethylurea; in Examples 50, 51 and 52 the urea-type compound was 5,5-dimethylhydantoin.

| Example | Parts of Urea-Type Compound (by weight) | Reaction Temperature, °C. | Reaction Time, hours | % NCO | Viscosity CPS/°C. |
|---------|------------------------------------------|---------------------------|----------------------|-------|-------------------|
| 47 | 1.5 | 100 | 1.0  | 29.5 | 55/26 |
| 48 | 2.0 | 100 | 0.5  | 28.9 | 34/53 |
| 49 | 3.0 | 100 | 0.25 | 28.2 | 39/53 |
| 50 | 1.5 | 200 | 1.0  | 28.9 | 40/53 |
| 51 | 2.0 | 200 | 1.0  | 29.0 | 37/67 |
| 52 | 3.0 | 200 | 0.5  | 28.5 | 40/69 |

EXAMPLES 53–54

In substantial accordance with the procedure described for Examples 42–46 an isocyanate blend containing 300 grams of isocyanate 1 and 300 grams of isocyanate 3 was reacted with either 36 grams of diethyl urea (Example 53) or 36 grams of dicyclohexyl urea (Example 54).

In the experiment of Example 53, the reaction mixture was heated at 100 degrees Centigrade for 2.0 hours until the NCO content of the reaction mixture was 27.0 percent; a product with a viscosity (at 25 degrees Centigrade) of 66 centipoises was obtained. In the experiment of Example 54, the reaction mixture was heated at 120 degrees Centigrade for 4.0 hours until the NCO content of the reaction mixture was 27.7 percent; a product with a viscosity (at 25 degrees Centigrade) of 70 centipoises was obtained.

EXAMPLE 55

A resin blend was prepared by mixing 200 parts (by weight) of polyol 2, 4.0 parts (by weight) of a catalyst solution consisting of a 1:3 (by weight) mixture of triethylene diamine and 1,4-butanediol, 40 parts (by weight) of 1,4-butanediol, and 0.04 parts (by weight) of dibutyltindilaurate. One hundred forty-four point six (144.6) parts (by weight) of the isocyanate of Example 42 and 200 parts of the resin blend were charged into a quart Plastikan and agitated with a high-speed drill fitted with a Cowles dissolver for 10 seconds. The system blend was poured quickly into an all-aluminum mold preheated to a temperature of 130–140 degrees Fahrenheit. After four minutes, the resulting solid pad was pulled from the mold and post-cured in an oven for one hour at a temperature of 250 degrees Fahrenheit. The solid pad was then aged for from about 3 to about 5 days at room temperature and thereafter evaluated.

The polyurethane foam of this Example had a density (pcf.) of 55.2; a tensile strength (p.s.i.) of 1720; an elongation (percent) of 120; a split tear (pounds per inch) of 115; a Graves tear (pounds per inch) of 323; a Shore D hardness (Inst./5 seconds) of 47/43; a heat sag (at 250 degrees Fahrenheit) of 0.34; a flexural recovery of 15/9; and flexural moduli (in thousands of pounds per square inch) of 43.17, 16.88, and 7.86 at minus 20 degrees Fahrenheit, 72 degrees Fahrenheit, and 150 degrees Fahrenheit, respectively.

EXAMPLES 56–97

In substantial accordance with the procedure described in Example 55, polyurethane foams prepared from the isocyanate of this invention were produced. A resin blend was prepared by mixing 100 parts (by weight) of a polyol, 2.0 parts (by weight) of a catalyst solution consisting of a 1:3 (by weight) mixture of triethylene diamine and 1,4-butanediol, 1,4-butanediol, and 0.02 parts (by weight) of dibutyltindilaurate. In Examples 56–65 and 77–87, 20 parts (by weight) of 1,4-butanediol were used; in Examples 66–76 and 88–97, 25 parts (by weight) of 1,4-butanediol were used. Polyol 2 was used in Examples 56–76; a 4000 molecular weight diol (polyol 3) was used in Examples 77–97. The isocyanates used in these experiments are described below.

| Example | Example Which Describes the Preparation of the Isocyanate Used in this Example | Amount of Isocyanate Used (parts by weight) |
|---|---|---|
| 56 | 43 | 79.6 |
| 57 | 44 | 74.0 |
| 58 | 47 | 63.9 |
| 59 | 48 | 65.3 |
| 60 | 49 | 66.9 |
| 61 | 45 | 70.9 |
| 62 | 46 | 73.4 |
| 63 | 50 | 65.3 |
| 64 | 51 | 65.1 |
| 65 | 52 | 66.2 |
| 66 | 42 | 84.3 |
| 67 | 43 | 92.8 |
| 68 | 44 | 86.4 |
| 69 | 47 | 74.6 |
| 70 | 48 | 76.1 |
| 71 | 49 | 77.9 |
| 72 | 45 | 84.6 |
| 73 | 46 | 85.6 |
| 74 | 50 | 76.1 |
| 75 | 51 | 75.8 |
| 76 | 52 | 77.2 |
| 77 | 42 | 72.6 |
| 78 | 43 | 79.6 |
| 79 | 44 | 74.4 |
| 80 | 47 | 64.2 |
| 81 | 48 | 65.6 |
| 82 | 49 | 67.2 |
| 83 | 45 | 71.3 |
| 84 | 46 | 73.7 |
| 85 | 50 | 65.6 |
| 86 | 51 | 65.3 |
| 87 | 52 | 66.4 |
| 88 | 43 | 93.1 |
| 89 | 44 | 86.6 |
| 90 | 47 | 74.8 |
| 91 | 48 | 76.3 |
| 92 | 49 | 78.2 |
| 93 | 45 | 84.7 |
| 94 | 46 | 85.8 |
| 95 | 50 | 76.3 |
| 96 | 51 | 76.0 |
| 97 | 52 | 77.4 |

The properties of the polyurethane foams of these examples are shown in Table I.

TABLE I

| Example | Density pcf. | Tensile Strength p.s.i. | Elong. % | Split Tear p.i. | Graves Tear p.i. | Shore D Inst./ 5 sec. | Heat Sag @ 250° F. | Flex Rec. | Flexural Modulus, p.s.i. × 10³ −20° F. | 72° F. | 150° F. |
|---|---|---|---|---|---|---|---|---|---|---|---|
| 56 | 54 | 1570 | 200 | 221 | 305 | 49/44 | 0.08 | 22/15 | 50.10 | 20.32 | 8.43 |
| 57 | 46 | 1300 | 180 | 150 | 233 | 48/39 | 0.42 | 20/13 | 45.47 | 15.85 | 6.22 |
| 58 | 61 | 2000 | 150 | 113 | 413 | 50/48 | 0.2 | 11/8 | 35.48 | 15.56 | 10.44 |
| 59 | 61 | 2010 | 140 | 123 | 378 | 48/42 | 0.16 | 10/7 | 37.53 | 17.30 | 11.32 |
| 60 | 61 | 1760 | 100 | 153 | 380 | 52/44 | 0.18 | 11/8 | 36.71 | 16.55 | 11.71 |
| 61 | 62 | 2040 | 140 | 143 | 360 | 52/49 | 0.38 | 9/5 | 53.68 | 18.17 | 9.58 |
| 62 | 62 | 1700 | 120 | 112 | 283 | 49/44 | 0.34 | 8/4 | 25.62 | 10.30 | 5.69 |
| 63 | 62 | 2020 | 140 | 143 | 356 | 51/44 | 0.20 | 10/7 | 35.83 | 23.24 | 10.71 |
| 64 | 65 | 1530 | 60 | 144 | 395 | 48/44 | 0.16 | 10/7 | 41.96 | 17.8 | 11.40 |
| 65 | 59 | 1790 | 100 | 128 | 379 | 48/44 | 0.16 | 11/6 | 42.35 | 16.73 | 11.55 |
| 66 | 57 | 2100 | 140 | 167 | 393 | 53/51 | 0.80 | 20/14 | 82.0 | 35.16 | 17.48 |
| 67 | 57 | 1900 | 140 | 216 | 431 | 56/52 | 0.88 | 74/15 | 85.21 | 37.00 | 19.13 |
| 68 | 57 | 1920 | 130 | 214 | 413 | 54/51 | 0.30 | 23/16 | 75.63 | 33.91 | 15.09 |
| 69 | 62 | 2400 | 120 | 153 | 429 | 53/47 | 0.28 | 12/8 | 57.90 | 28.04 | 17.79 |
| 70 | 66 | 2250 | 110 | 186 | 403 | 54/44 | 0.18 | 10/6 | 54.80 | 26.00 | 17.74 |
| 71 | 60 | 2180 | 80 | 176 | 401 | 46/43 | 0.20 | 13/8 | 53.91 | 27.05 | 19.64 |
| 72 | 52 | 1700 | 70 | 105 | 271 | 50/45 | 0.16 | 11/6 | 51.14 | 22.64 | 13.70 |
| 73 | 53 | 1970 | 100 | 120 | 298 | 51/44 | 0.20 | 16/10 | 52.80 | 21.59 | 11.96 |
| 74 | 62 | 2500 | 120 | 179 | 434 | 49/46 | 0.16 | 10/5 | 60.87 | 28.11 | 18.08 |
| 75 | 63 | 2400 | 110 | 168 | 529 | 53/48 | 0.20 | 10/5 | 64.35 | 29.91 | 18.78 |
| 76 | 62 | 2450 | 120 | 190 | 481 | 52/47 | 0.14 | 11/7 | 67.61 | 28.52 | 18.37 |
| 77 | 57 | 1520 | 200 | 211 | 338 | 48/43 | 0.76 | 12/7 | 50.40 | 16.52 | 6.65 |
| 78 | 54 | 1300 | 150 | 137 | 275 | 47/41 | 1.36 | 16/10 | 48.54 | 15.43 | 5.53 |
| 79 | 60 | 1320 | 100 | 168 | 356 | 54/42 | 0.34 | 19/11 | 73.04 | 27.69 | 8.24 |
| 80 | 65 | 1810 | 190 | 373 | 476 | 47/36 | 0.28 | 8/5 | 32.77 | 14.01 | 8.74 |
| 81 | 65 | 1700 | 150 | 225 | 395 | 43/32 | 0.34 | 6/5 | 30.59 | 11.48 | 7.54 |
| 82 | 64 | 1180 | 80 | 208 | 306 | 41/29 | 0.50 | 8/4 | 23.64 | 7.69 | 5.15 |
| 83 | 55 | 1500 | 140 | 136 | 298 | 48/43 | 0.52 | 13/8 | 44.48 | 15.94 | 7.65 |
| 84 | 59 | 1180 | 60 | 120 | 255 | 44/34 | 0.44 | 10/5 | 29.26 | 10.64 | 6.78 |
| 85 | 63 | 1990 | 200 | 188 | 460 | 49/38 | 0.26 | 6/3 | 36.30 | 14.19 | 9.11 |
| 86 | 64 | 2080 | 210 | 229 | 480 | 41/32 | 0.32 | 5/2 | 33.04 | 13.60 | 9.11 |
| 87 | 66 | 2100 | 220 | 279 | 529 | 48/44 | 0.46 | 7/3 | 39.86 | 14.89 | 9.32 |
| 88 | 58 | 1530 | 70 | 212 | 393 | 56/51 | 0.64 | 29/19 | 104.01 | 35.36 | 12.23 |
| 89 | 57 | 1590 | 160 | 260 | 418 | 54/52 | 0.70 | 18/10 | 90.39 | 30.59 | 11.90 |
| 90 | 63 | 2050 | 130 | 281 | 495 | 53/45 | 0.26 | 11/5 | 52.44 | 21.01 | 12.64 |
| 91 | 65 | 2250 | 150 | 233 | 516 | 54/49 | 0.26 | 10/6 | 53.91 | 23.20 | 14.86 |
| 92 | 60 | 1690 | 80 | 243 | 416 | 53/45 | 0.22 | 11/6 | 53.62 | 20.55 | 12.05 |
| 93 | 54 | 2000 | 120 | 137 | 354 | 52/48 | 0.26 | 12/6 | 59.25 | 25.94 | 13.73 |
| 94 | 54 | 1800 | 130 | 118 | 299 | 50/42 | 0.1 | 10/5 | 43.4 | 15.7 | 8.7 |
| 95 | 64 | 2300 | 170 | 288 | 555 | 53/45 | 0.16 | 9/5 | 64.84 | 25.44 | 14.38 |
| 96 | 65 | 2290 | 160 | 296 | 500 | 54/49 | 0.22 | 7/3 | 63.36 | 25.84 | 15.87 |

TABLE I-continued

| Example | Density pcf. | Tensile Strength p.s.i. | Elong. % | Split Tear p.i. | Graves Tear p.i. | Shore D Inst./ 5 sec. | Heat Sag @ 250° F. | Flex Rec. | Flexural Modulus, p.s.i. × 10³ | | |
|---|---|---|---|---|---|---|---|---|---|---|---|
| | | | | | | | | | −20° F. | 72° F. | 150° F. |
| 97 | 62 | 2110 | 170 | 315 | 563 | 43/45 | 0.24 | 10/5 | 66.65 | 24.60 | 14.50 |

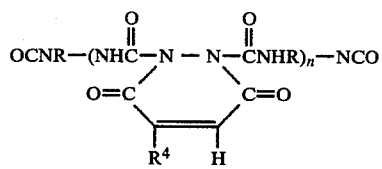

COMPARATIVE EXAMPLES 98–101

In substantial accordance with the procedure described in Example 55, polyurethane foams derived from iso cyanate 3 were prepared. In each of these Examples, the specified amounts of isocyanate 3 were reacted with a resin blend prepared from 100 parts (by weight) of polyol, 1,4-butanediol, 2.0 parts (by weight) of a catalyst solution consisting of a 1:3 (by weight) mixture of triethylene diamine and 1,4-butanediol, and 0.02 parts (by weight) of dibutyltindilaurate. In Examples 98 and 100, 20 parts (by weight) of 1,4-butanediol were used; in Examples 99 and 101, 25 parts (by weight) of 1,4-butanediol were used. Sixty-three point four (63.4), 78.4, 77.8, and 78.6 parts of isocyanate 3 were used in Examples 98, 99, 100, and 101, respectively. Polyol 2 was used in Examples 98 and 99; polyol 3 was used in Examples 100 and 101.

The properties of the polyurethane foams of these experiments are described below.

| | 98 | 99 | 100 | 101 |
|---|---|---|---|---|
| Density, pcf. | 68 | 64 | 64 | 63 |
| Tensile strength, p.s.i. | 2270 | 2380 | 2170 | 2480 |
| Elongation, percent | 70 | 50 | 110 | 70 |
| Split tear, p.i. | 79 | 100 | 130 | 140 |
| Graves tear, p.i. | 312 | 394 | 400 | 441 |
| Shore D hardness, Inst./5 sec. | 54/59 | 60/52 | 57/47 | 58/53 |
| Heat sag at 250° F. | 0.68 | 0.54 | 0.34 | 0.36 |
| Flex recovery | 12/9 | 16/11 | 12/9 | 14/9 |
| Flex modulus, p.s.i. × 10³ | | | | |
| −20° F. | 49.42 | 71.53 | 51.90 | 96.09 |
| 72° F. | 22.34 | 35.30 | 23.41 | 34.47 |
| 150° F. | 15.29 | 22.65 | 15.27 | 23.10 |

The use of the isocyanate of this invention in the polyurethane foams of Examples 45–65 improved the tear strength, heat sag, and flexural modulus properties of the foam; compare the properties of these foams with those of the foam of Example 98. The use of said isocyanate in the foams of Examples 66–76 improved their elongation, tear strength, heat sag, and flexural modulus properties. The polyurethane foams of Examples 77–87 and 88–97 demonstrate improved elongation and tear strength properties.

Although the invention has been described in considerable detail in this specification, it is to be understood that such detail is solely for the purpose of illustration and that many variations may be made by those skilled in the art without departing from the spirit and scope of the invention.

The embodiments of this invention in which an exclusive privilege or property is claimed are as follows:

1. A carbamylbiuret-modified polyisocyanate of the formula:

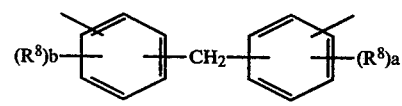

wherein n is an integer of from about 1 to about 20; R is a divalent hydrocarbon radical containing from about 1 to about 18 carbon atoms; and R⁴ is selected from the group consisting of hydrogen, alkyl containing from about 1 to about 6 carbon atoms, cycloalkyl containing from about 3 to about 7 carbon atoms, phenyl and benzyl.

2. The carbamylbiuret-modified polyisocyanate of claim 1, wherein R is an aromatic divalent radical containing from about 6 to about 15 carbon atoms.

3. The carbamylbiuret-modified polyisocyanate of claim 2, wherein said R is

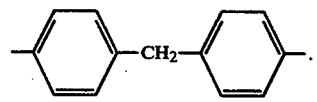

and $R^8$ is methyl and a and b are integers of from 0 to 2.

4. The carbamylbiuret-modified polyisocyanate of claim 3, wherein said R is

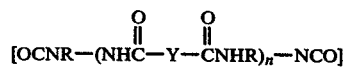

5. A carbamylbiuret-modified polyisocyanate of the formula:

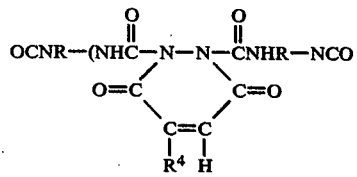

wherein n is an integer of from about 1 to about 20; R is a divalent hydrocarbon radical containing from about 1 to about 18 carbon atoms: wherein $R^4$ is selected from the group consisting of hydrogen, alkyl containing from about 1 to about 6 carbon atoms, cycloalkyl containing from about 3 to about 7 carbon atoms, phenyl, and benzyl wherein said polyisocyanate contains from about 2 to about 50 percent by weight of the polyisocyanate of carbodiimide-containing species.

6. The polyisocyanate of claim 5, wherein R is an aromatic divalent radical containing from about 6 to about 15 carbon atoms.

* * * * *

UNITED STATES PATENT AND TRADEMARK OFFICE
CERTIFICATE OF CORRECTION

PATENT NO. : 4,331,809
DATED : May 25, 1982
INVENTOR(S) : Donald L. Christman and Peter T. Kan It is certified that error appears in the above—identified patent and that said Letters Patent is hereby corrected as shown below: Claim 5 should read as follows:

A carbamylbiuret-modified polyisocyanate of the formula:

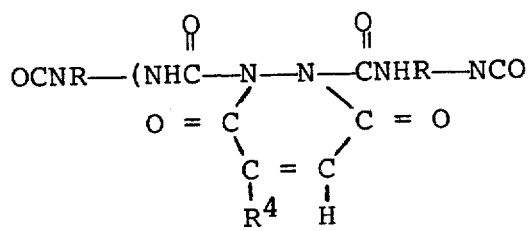

wherein n is an integer of from about 1 to about 20; R is a divalent hydrocarbon radical containing from about 1 to about 18 carbon atoms: wherein $R^4$ is selected from the group consisting of hydrogen, alkyl containing from about 1 to about 6 carbon atoms, cycloalkyl containing from about 3 to about 7 carbon atoms, phenyl, and benzyl wherein said polyisocyanate contains from about 2 to about 50 percent by weight of the polyisocyanate of carbodiimide-containing species.

Signed and Sealed this

Tenth Day of August 1982

[SEAL]

Attest:

Attesting Officer

GERALD J. MOSSINGHOFF
Commissioner of Patents and Trademarks